United States Patent
Katafuchi et al.

(10) Patent No.: US 6,562,212 B2
(45) Date of Patent: May 13, 2003

(54) GAS SENSOR ELEMENT

(75) Inventors: Tooru Katafuchi, Kariya (JP); Yasumichi Hotta, Mie-ken (JP); Namitsugu Fujii, Yokkaichi (JP)

(73) Assignee: Denso Corporation, Aichi-pref. (JP)

( * ) Notice: Subject to any disclaimer, the term of this patent is extended or adjusted under 35 U.S.C. 154(b) by 0 days.

(21) Appl. No.: 09/916,344

(22) Filed: Jul. 30, 2001

(65) Prior Publication Data
US 2002/0011411 A1 Jan. 31, 2002

(30) Foreign Application Priority Data
Jul. 31, 2000 (JP) ........................... 2000-231821

(51) Int. Cl.$^7$ ............................. G01N 27/407
(52) U.S. Cl. ................. 204/427; 204/426; 204/429
(58) Field of Search ................. 204/424, 425, 204/426, 427, 428, 429

(56) References Cited

U.S. PATENT DOCUMENTS

| | | | |
|---|---|---|---|
| 4,136,000 A | 1/1979 | Davis et al. | |
| 4,169,777 A | 10/1979 | Young et al. | |
| 4,294,668 A | 10/1981 | Young | |
| 5,173,167 A | * 12/1992 | Murase et al. | ............. 204/426 |
| 5,948,225 A | * 9/1999 | Katafuchi et al. | ............. 204/421 |
| 6,306,457 B1 | * 10/2001 | Schneider et al. | ............. 204/429 |

FOREIGN PATENT DOCUMENTS

| | | |
|---|---|---|
| JP | 55-39096 | 3/1980 |
| JP | 55-39097 | 3/1980 |
| JP | 5-18938 | 1/1993 |

OTHER PUBLICATIONS

Compilation of ASTM Standard Definitions, 4th Ed., p. 300, 1979.*

* cited by examiner

Primary Examiner—Robert J. Warden, Sr.
Assistant Examiner—Kaj K. Olsen
(74) Attorney, Agent, or Firm—Nixon & Vanderhye PC (57) ABSTRACT

A gas sensor element is provided which is used in a gas sensor such as an oxygen sensor. The gas sensor element includes a solid electrolyte body, a target gas electrode provided on a surface of the solid electrolyte body so as to be exposed to a gas to be measured, and a reference gas electrode provided on a surface of the solid electrolyte body so as to be exposed to a reference gas. Each of the target gas electrode and the reference gas electrode is made up of a plurality of crystal grains defined by grain boundaries. The total length of the grain boundaries in each of the target gas electrode and the reference gas electrode is 1000 $\mu$m or more in a surface area of 1000 $\mu m^2$. This ensures a sufficient degree of diffusion of the gasses in the target and reference gas electrodes, thereby providing a rapid response rate to the gas sensor element.

4 Claims, 6 Drawing Sheets

GAS SENSOR ELEMENT

BACKGROUND OF THE INVENTION

1. Technical Field of the Invention

The present invention relates generally to a sensor element of a gas sensor which may be employed in air-fuel ratio control of internal combustion engines.

2. Background Art

A typical gas sensor to be disposed in an exhaust system of an internal combustion engine for controlling the air-fuel ratio has a sensor element which consists essentially of a solid electrolyte body, a target gas electrode, and a reference gas electrode.

The target gas electrode is disposed within a gas chamber filled with a gas to be measured and generally has a protective layer formed on an outer surface thereof. The protective layer is usually made of a porous ceramic material.

The solid electrolyte body is usually made of an oxygen ion conductive material such as a ceramic material which is produced by forming and baking $ZrO_2$ powder.

The target gas electrode and the reference gas electrode are exposed to the gas to be measured and a reference gas such as air, respectively, and produce an output as a function of the concentration of a specific component contained in the gas such as oxygen. The measurement of the specific component may be achieved by applying the voltage to each of the target gas electrode and the reference gas electrode or in another known manner.

The target gas and reference gas electrodes are each designed to perform a catalyst function to facilitate average reaction of the gas to be measured, which enables, for example, the concentration of oxygen contained in exhaust gasses of the internal combustion engine to be measured with high accuracy for determination of the stoichiometric.

Typically, each of the target gas electrode and the reference gas electrode is made in (1) a chemically plating manner or (2) a baking manner in which a paste containing an electrode material is applied to a solid electrolyte body and baked.

In the former manner (1), in order to avoid aggravation or cohesion caused by exposure to the heat during use of the gas sensor, after plated, the electrode needs to be subjected to heat treatment at a temperature higher than that to which the gas sensor is exposed actually.

In the latter manner (2), the solid electrolyte body to which the paste is applied is baked usually at temperatures of 1300 to 1500° C.

It is known in the art that the above heat treatment and baking result in inactivation of the electrode, which will lead to a decrease in response of the sensor element. In order to avoid this drawback and to improve electrode response, it has been proposed to expose the electrode to a strong reducing atmosphere with $H_2$ or CO treatment to highly activate the electrode.

In recent years, however, the emission regulations have been made more rigorous, and burn control gas sensors installed in an exhaust system of an internal combustion engine are required to have their response increased more than before.

The improvement of the response by the above reducing treatment has its limit. Another method of increasing the response of the sensor element is, therefore, sought.

The improvement of the response rate of the gas sensor may also be achieved by forming a large number of pores in a protective layer provided on the electrode to improve the degree of diffusion of the gas. The protective layer, however, must be designed to protect the electrode against noxious compositions contained in the gas to be measured as well as avoidance of thermal cohesion. Usually, exhaust gasses within an exhaust pipe of an internal combustion engine contain much poison such as Pb compounds produced from gasoline and Si compounds generated from the exhaust pipe. The protective layer will facilitate ease of penetration of the poison through the protective layer to the electrode, thus resulting in premature deterioration of the electrode.

SUMMARY OF THE INVENTION

It is therefore a principal object of the invention to avoid the disadvantages of the prior art.

It is another object of the invention to provide a gas sensor element which exhibits a rapid response and a higher heat resistance.

According to one aspect of the invention, there is provided a gas sensor element which comprises: (a) a solid electrolyte body; (b) a target gas electrode provided on a surface of the solid electrolyte body so as to be exposed to a gas to be measured; and (c) a reference gas electrode provided on a surface of the solid electrolyte body so as to be exposed to a reference gas. Each of the target gas electrode and the reference gas electrode is made up of a plurality of crystal grains defined by grain boundaries. The total length of the grain boundaries in each of the target gas electrode and the reference gas electrode is 1000 $\mu$m or more in a surface area of 1000 $\mu m^2$.

In the preferred mode of the invention, the number of pores formed in the target gas electrode whose diameters are within a range of 0.1 $\mu$m to twice the thickness of the target gas electrode are 5 to 100 in a surface area of 1000 $\mu m^2$.

The number of pores formed in the reference gas electrode whose diameters are within a range of 0.1 $\mu$m to twice the thickness of the reference gas electrode are 5 to 100 in a surface area of 1000 $\mu m^2$.

Some of the pores exist in grain boundaries of each of the target gas electrode and the reference gas electrode.

According to another aspect of the invention, there is provided a method of producing a gas sensor element which includes a solid electrolyte body, a target gas electrode provided on a surface of the solid electrolyte body so as to be exposed to a gas to be measured, and a reference gas electrode provided on a surface of the solid electrolyte body so as to be exposed to a reference gas. The method comprises the steps of exposing the gas element to a gas atmosphere containing at least one of a hydrocarbon gas, a CO gas, and a $H_2$ gas at 400 to 900° C. and applying an ac voltage to the target gas electrode and the reference gas electrode. This causes pores to be formed in the target gas electrode and the reference gas electrode.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
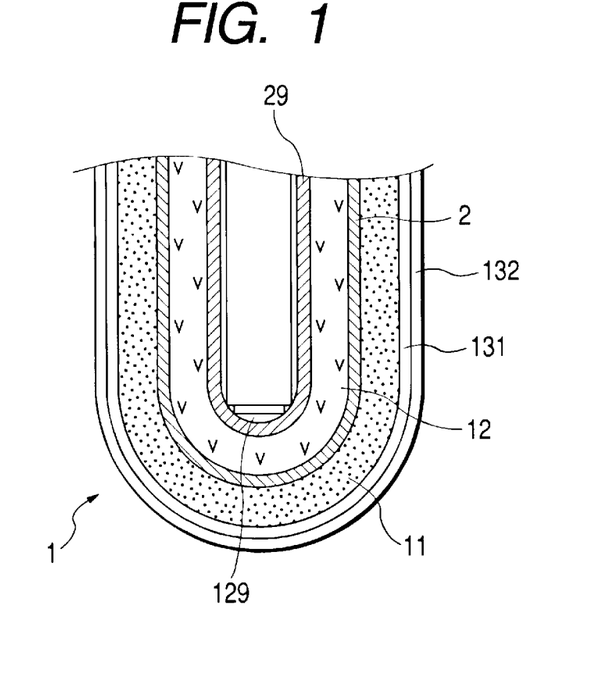
FIG. 1 is a partially sectional view which shows a gas sensor element according to the invention.
Figure 2:
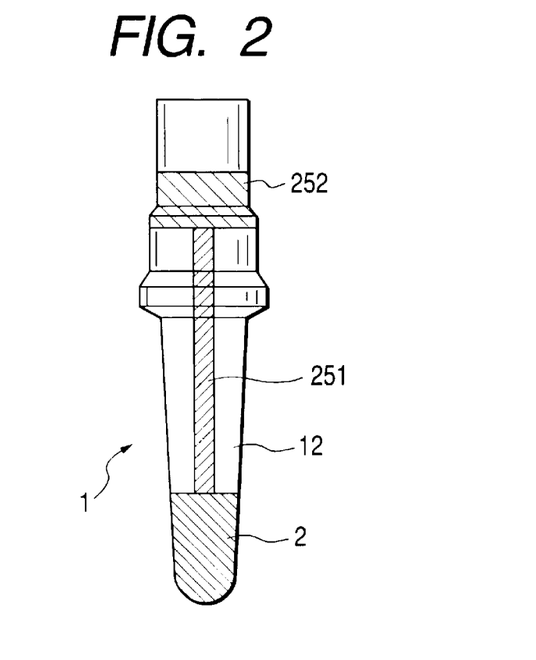
FIG. 2 is a perspective view which shows a gas sensor element according to the invention.

Referring to the drawings, wherein like reference numbers refer to like parts in several views, particularly to FIGS. 1 and 2, there is shown a gas sensor element 1 according to the invention.

The gas sensor element 1 consists essentially of a hollow solid electrolyte body 12, a target gas electrode 2, and a reference gas electrode 29. The target gas electrode 2 is formed on an outer surface of the solid electrolyte body 12 and exposed to a gas to be measured. The reference gas electrode 29 is formed on an inner surface of the solid electrolyte body 12 and exposed to a reference gas such as air.

Figure 3A:
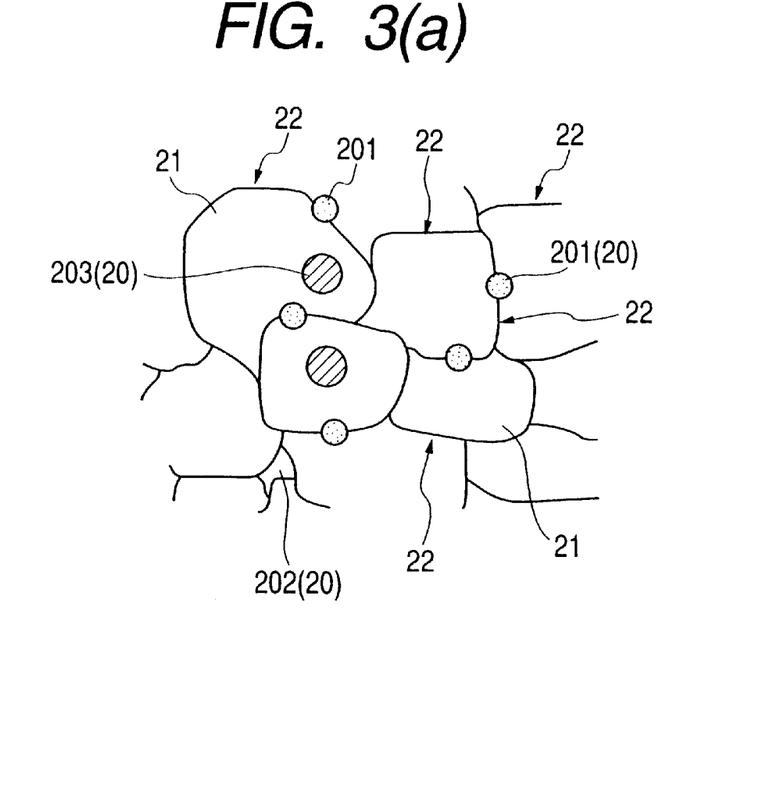
FIG. 3(a) is a view which shows a crystal structure of a gas sensor element.

Each one of the target gas electrode 2 and the reference gas electrode 29 is, as clearly shown in FIG. 3(a), made from many crystal grains 21. There are grain boundaries 22 between the crystal grains 21. The total length of the boundaries 22 in a surface area of 1000 $\mu m^2$ (i.e., the sum of lengths of the grain boundaries) is 1000 $\mu m$ or more.

Figure 4:
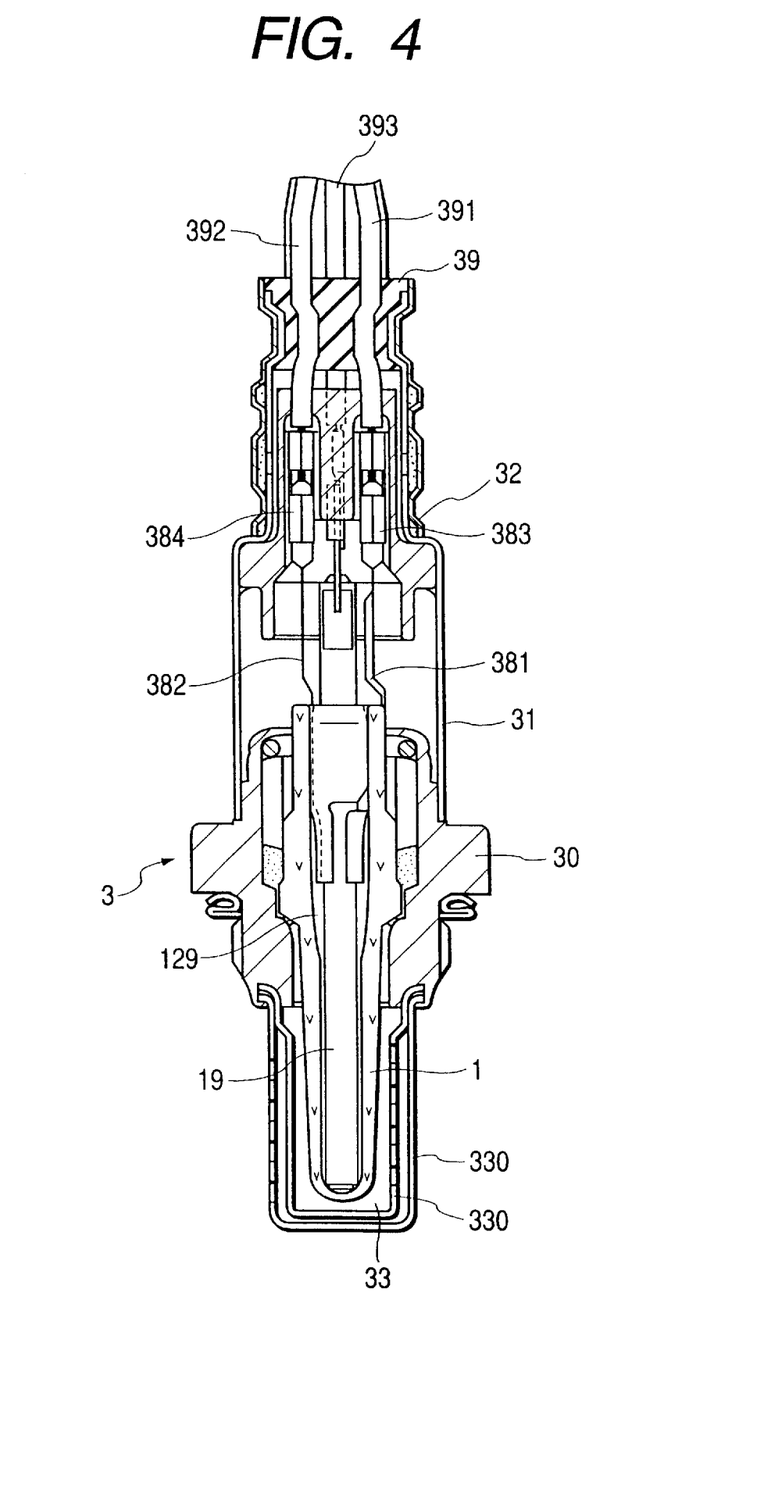
FIG. 4 is a vertical sectional view which shows a gas sensor in which the gas sensor element of FIGS. 1 and 2 may be installed.

The gas sensor element 1 may be installed in an oxygen sensor 3, as shown in FIG. 4, which is disposed in an exhaust pipe of an internal combustion engine to measure the oxygen content of exhaust gasses for engine burning control.

Referring back to FIGS. 1 and 2, the solid electrolyte body 12 has formed therein a reference gas chamber 129 filled with air as the reference gas. The target gas electrode 2 has formed thereon a protective layer 11 which is covered with second and third protective layers 131 and 132. The second protective layer 131 is provided for enhancing the effect of trapping harmful compositions of the exhaust gasses of the engine. The second protective layer 131 is made mainly from $Al_2O_3$ and has a thickness of 120 $\mu m$ and a porosity of 20 to 50%.

The third protective layer 132 has a porosity greater than that of the second protective layer 131 to trap poisonous compositions of the exhaust gasses greater in size than those trapped in the second protective layer 131 for avoiding the jamming of the second protective layer 131. The third protective layer 132 is made mainly from $Al_2O_3$ and has a thickness of 40 $\mu m$ and a porosity of 60%.

The target gas electrode 2 and the reference gas electrode 29 are each made from a platinum material. The gas sensor element 1 has lead electrodes and terminal electrodes formed in the outer and inner surfaces thereof which are electrically connected to the target gas electrode 2 and the reference gas electrode 29 for applying the voltage thereto. FIG. 2 shows only the lead electrode 251 and the terminal electrode 252 formed on the outer surface of the gas sensor element 1 for the sake of simplicity of illustration.

The surface of each of the target gas electrode 2 and the reference gas electrode 29 is, as described above with reference to FIG. 3(a), made of a large number of the platinum crystal grains 21 and has many pores 20 formed therein. The pores 20 may be broken down into three groups: (1) grain boundary pores 201 existing in the grain boundaries 22, (2) triple pores 202 defined by gaps each formed by side walls of more than two adjacent crystal grains 21, and (3) in-grain pores 203 existing inside the crystal grains 21.

The grain boundary pores 201 and the triple pores 20 formed in each of the target gas electrode 2 and the reference gas electrode 29 whose diameters are between 0.1 $\mu m$ and twice the average thickness of the target gas electrode 2 and the reference gas electrode 29 are 5 to 100 in a surface area of 1000 $\mu m^2$.

The oxygen gas sensor 3 includes, as shown in FIG. 4, a hollow cylindrical housing 30 within which the gas sensor element 1 is disposed, air covers 31 and 32, and a protective cover assembly consisting of an outer and an inner cover 330. The protective cover assembly is installed on a head of the housing 30 to define a gas chamber 33 into which a gas to be measured is admitted through gas holes formed in the outer and inner covers 330. The air cover 32 is installed around the air cover 31. The air cover 31 is installed on a flange of the housing 30.

The gas sensor element 1 has defines therein a reference gas chamber 129 into which air is admitted as the reference gas. Within the reference gas chamber 129, a ceramic bar heater 19 is disposed which heats the gas sensor element 1 up to a suitable temperature for measuring the gas. The heater 19 is retained within the reference gas chamber 129 with a given gap between itself and an inner wall of the gas sensor element 1 and has a head contact with the inner wall of the gas sensor element 1.

Fitted within an open end of the air cover 31 is an insulating rubber 39 which retains therein leads 391 to 393. The leads 391 and 392 are connected electrically to the gas sensor element 1 through connectors 383 and 384 coupled with terminals 381 and 382 installed on the gas sensor element 1 for applying the voltage to and picking up a sensor signal from the gas sensor element 1. The terminals 381 and 382 are in contact with the terminal electrode 252, as shown in FIG. 2. The leads 393 (only one is shown for the sake of simplicity of illustration) are connected to the heater 19 for power supply. For a more detailed structure and operation of the oxygen gas sensor 3, reference is made to U.S. application Ser. No. 09/196,693 filed on Nov. 20, 1998, now U.S. Pat. No. 6,222,372, assigned to the same assignee as that of this application, disclosure of which is incorporated herein by reference.

The production of the gas sensor element is accomplished in the following steps.

First, the cut-shaped solid electrolyte body 12 made from a $ZrO_2$-based ceramic material is prepared.

A paste containing 0.4 Wt % of dibenzylidene Pt (organic noble metal compound), as expressed in quantity of a noble metal, is applied to the outer surface of the solid electrolyte body 12 using pad printing techniques. This is a process prior to plating. Next, the solid electrolyte body 12 is heated at 300° C. to remove a binder used.

Usually, the decomposition of an organic noble metal requires heat of more than 700° C., but such heat may cause the core of the noble metal to be cohered, which results in the formation of pores in the electrode (i.e., the target gas electrode 2 or the reference has electrode 29) after plating or an increase in the size of crystal grains of the electrode. In order to avoid this drawback, this embodiment uses an organic noble metal compound and a binder which are decomposable at lower temperatures to keep the core of the organic noble metal compound fine or highly dense.

The solid electrolyte body 12 is plated with a plating liquid containing a Pt complex at 35° C. which is higher than a standard plating temperature for avoiding an increase in plated grain caused by a drop in plating speed.

The solid electrolyte body 12 is subjected to a heat treatment at 1100° C. in air to produce the target gas electrode 2 shown in FIG. 2. The lead electrode 251 and the terminal electrode 252 are also formed in the above processes.

The reference gas electrode 29 is formed in the same manner as described above.

Afterwards, the protective layer 11 is formed on the solid electrolyte body 12 through spinel injection.

The solid electrolyte body 12 is dipped in a slurry of $Al_2O_3$ and then heated to form the second protective layer 131. The third protective layer 132 is also formed on the second protective layer 131 in the same manner.

Figure 3B:
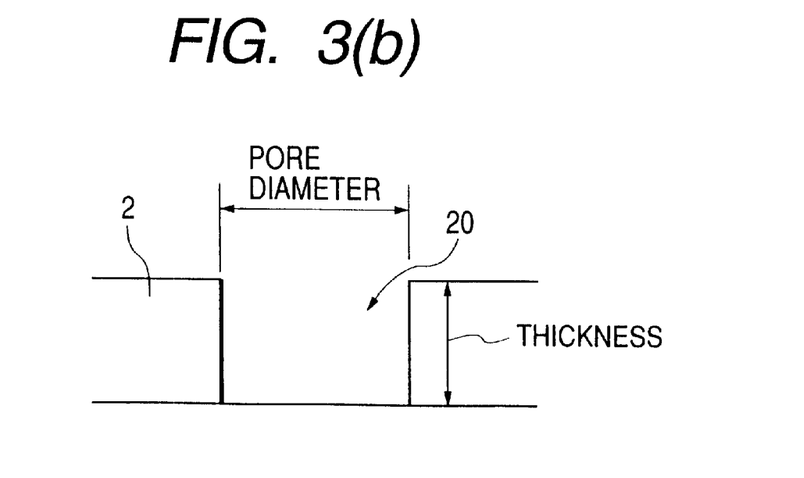
FIG. 3(b) is a sectional view which shows a pore.

We captured an image of the surface of each of the target gas electrode 2 and the reference gas electrode 29 formed on the solid electrolyte body 12 in the above manner using a scan type electron microscope and picked up the grain boundaries 22, as shown in FIG. 3(a), from the image using an image recognizing device to measure the total length of the grain boundaries 22 in an area of 1000 $\mu m^2$. The grain boundaries 22 are defined by interfaces formed between the adjacent crystal grains 21. The in-grain pores 203 are, as can be seen from FIG. 3(a), not produced in the grain boundaries 22. One example of the pores 22 is illustrated in FIG. 3(b).

The grain boundaries 22 were measured in four areas within a surface range of 1 $mm^2$ of each of the target gas electrode 2 and the reference gas electrode 29. The results of the measurements showed that the total length of the grain boundaries 22 in each area were on the order of 2000 $\mu m$.

We also found the relation between the total length of the grain boundaries and the response rate of the gas sensor element 1 in the following manner.

A plurality of test gas sensor elements were prepared using chemical plating techniques. Measuring the total length of grain boundaries of each of the test gas sensor elements, it was found that a variation in total length of the grain boundaries was in a range of 250 to 3000 $\mu m$.

Figure 5:
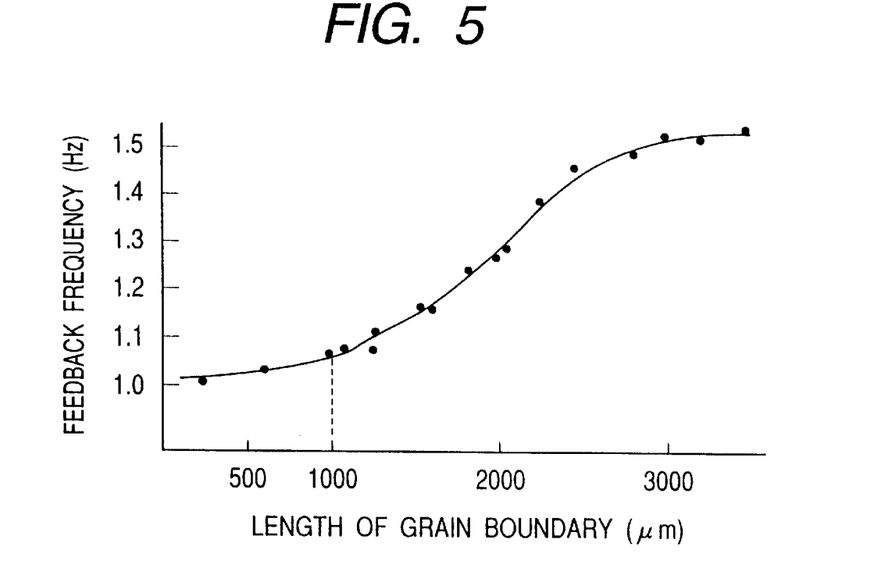
FIG. 5 is a graph which shows a relation between a feedback frequency of a sensor output and a total length of grain boundaries.

The test gas sensor elements were each built in the oxygen gas sensor 3 shown in FIG. 4 and installed in an exhaust system of an automotive engine. The engine was operated to discharge exhaust gasses of 400° C. to the exhaust system. An output of each of the test gas sensor elements was produced under feedback control and measured. The results of the measurements are listed in FIG. 5. The ordinate axis indicates the feedback frequency of the outputs of the test gas sensor elements. The abscissa axis indicates the total length of the grain boundaries 22. The graph shows that the feedback frequency of the output of the test gas sensor elements reaches 1.065 Hz when the total length of the grain boundaries 22 exceeds 1000$\mu$. Specifically, it is found that the inclination of a curve indicative of the feedback frequency starts to increase greatly when the total length of the grain boundaries 22 exceeds 1000 $\mu m$, so that the diffusion of each of the target gas and the reference gas within a corresponding one of the target gas electrode 2 and the reference gas electrode 29 through the gain boundaries 22 reflects on the output of the gas sensor element 1 greatly, thereby resulting in an improved response of the gas sensor element 1.

Figure 6:
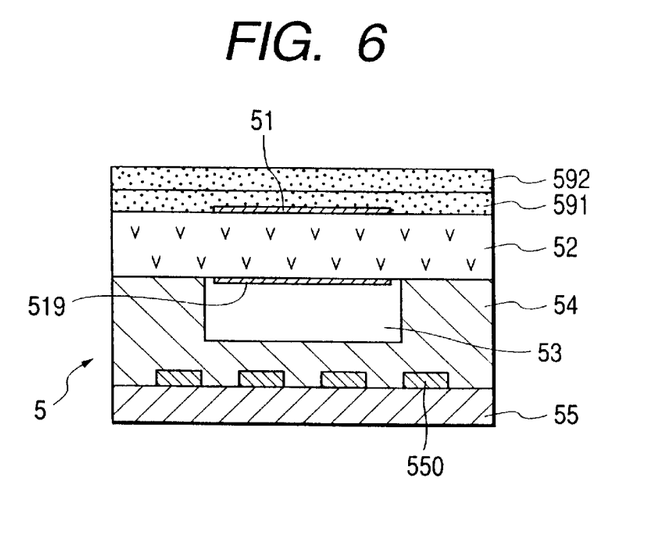
FIG. 6 is a sectional view which shows a laminated gas sensor element with which the invention may be employed.

The above embodiment may also be used with a laminated gas sensor element 6, as shown in FIG. 6. For example, U.S. Pat. No. 5,573,650, issued on Nov. 12, 1996 to Fukaya et al. teaches a typical laminated sensor element, disclosure of which is incorporated herein by reference.

The laminated gas sensor element 6 consists of a solid electrolyte plate 52, a target gas electrode 51, and a reference gas electrode 519 which are formed on the solid electrolyte plate 52. A heater substrate 55 on which a heater 550 is formed and a spacer 54 are laid on one of surfaces of the solid electrolyte plate 52. A first protective layer 591 and a second protective layer 592 are formed on the other surface of the solid electrolyte plate 52.

The solid electrolyte plate 52 is made from a $ZrO_2$-based ceramic material The heater substrate 55 and the spacer 54 are each produced by a ceramic sheet made from $Al_2O_3$ using press or injection molding techniques or sheet forming techniques using, for example, a doctor blade.

Lead and terminal electrodes (not shown) are formed on an outer surface of the gas sensor element 5 in electric communication with the target gas electrode 51 and the reference gas electrode 519, respectively. Other arrangements are identical with those in the gas sensor element 1, and explanation thereof in detail will be omitted here.

The above embodiment may also be used with a two-cell laminated gas sensor element made up of a plurality of solid electrolyte bodies and a large number of electrodes formed on the solid electrolyte bodies and with a NOx sensor element made of a NOx activatable material.

The second embodiment will be described below.

After being plated in the chemical manner as described above, the target gas electrode 2 may be subjected to the following electric process to adjust the number of pores formed therein.

Figure 7:
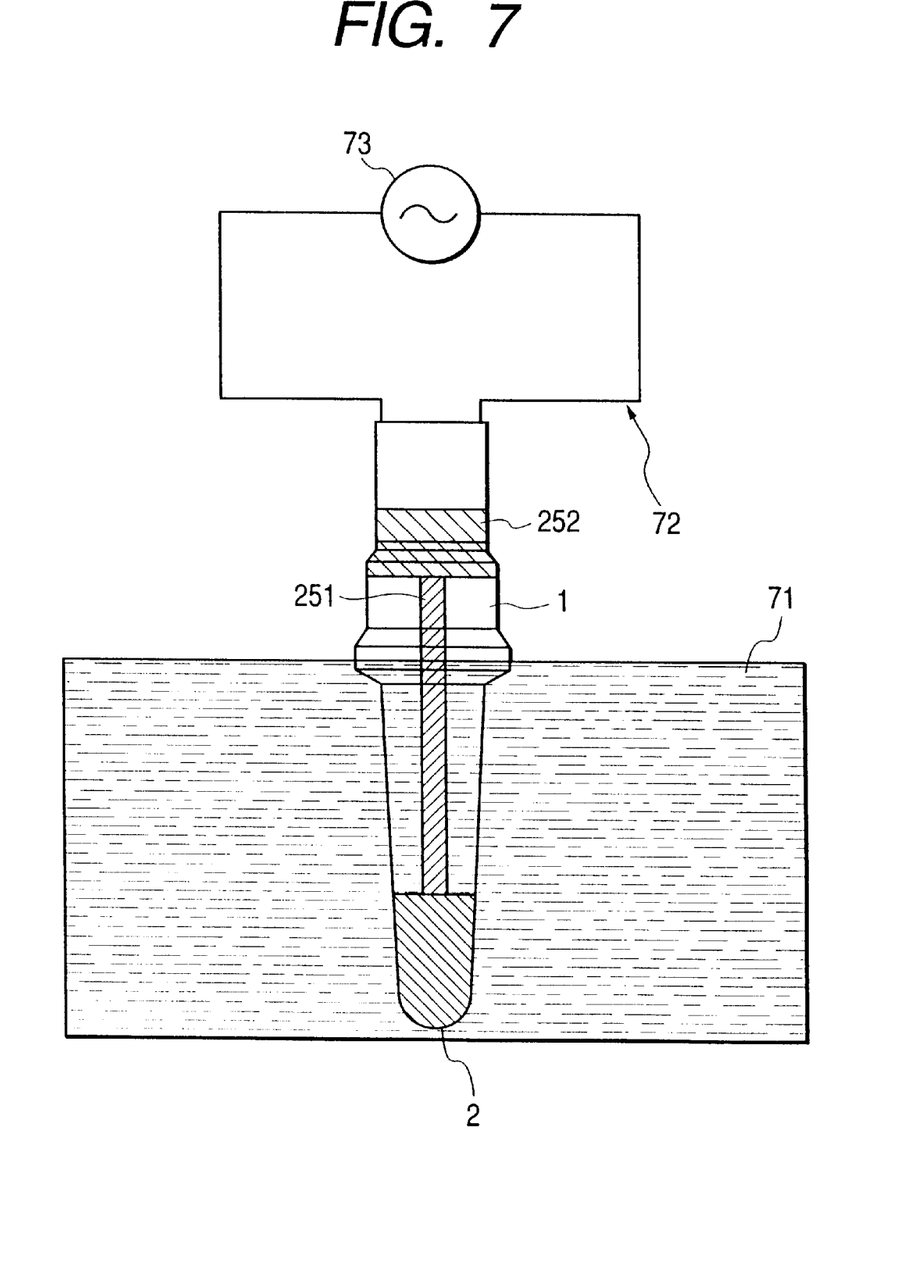
FIG. 7 is a view which shows a gas sensor element according to the second embodiment of the invention.

First, the target gas electrode 2 is, as shown in FIG. 7, exposed to a gas atmosphere 71 containing at least one of a hydrocarbon gas, a CO gas, and a $H_2$ gas such as a coal gas or a petroleum gas at 400 or 900°, e.g., 700° C. The temperature of the gas sensor element 1 is kept at 700° C. As the hydrocarbon gas, a methane gas or a commercial propane may be used. In this embodiment, the gas atmosphere 71 contained $H_2$ and $O_2$ of 10:8 in equivalent ratio.

Next, a voltage source circuit 72 having an ac power supply 73 is connected to the terminal electrode 252 leading to the target gas electrode 2 and the terminal electrode (not shown) leading to the reference gas electrode 29. The ac voltage whose frequency is 1 Hz or more and amplitude is ±0.1V to ±5.0V, e.g., ±2.0V is applied to the target gas electrode 2 and the reference gas electrode 29 for 30 minutes. This causes the pores in the target gas electrode 2 to increase. The result of our test showed that the pores in a surface area of 1000 $\mu m^2$ of the target gas electrode 2 increased from three (3) to fifty two (52). Specifically, in the gas atmosphere 71, oxygen molecules exist which are coupled weakly to the surface of the target gas electrode 2. The application of the ac voltage to the gas sensor element 1 causes the oxygen molecules to be connected to and disconnected from the surface of the target gas electrode 2 cyclically, thereby causing pores to be formed in the target gas electrode 2. If the ac voltage is applied to the gas sensor element 1 below 400° C., the catalytic activity of each of the target gas electrode 2 and the reference gas electrode 29 is low, thus resulting in a difficulty in connection and disconnection of the oxygen molecules to and from the surface of the target gas electrode 2. Alternatively, if the ac voltage is applied to the gas sensor element 2 above 900° C., it may cause the gas compositions in the gas atmosphere 71 to disappear before reaching the target gas electrode 2. If the amplitude of the voltage to be applied to the gas sensor element 1 is less than ±0.1V, it is difficult to provide a sufficient activation energy to facilitate the formation of the pores. Alternatively, if the amplitude is more than ±5.0V, it causes the gas sensor element 1 to be browned, thus resulting in a decrease in strength of the gas sensor element 1.

The number of pores formed in the reference gas electrode 29 may also be adjusted in the same manner as described above.

As an alternative to the above electrical process, the adjustment of the number of pores in each of the target gas electrode 2 and the reference gas electrode 29 may be achieved by a heat treatment or adjustment of diameter of grains in a core of a noble metal contained therein.

We performed sensor performance tests in terms of the response rate and the heat resistance in relation to the number of pores. A plurality of test gas sensor elements were prepared which were made by the chemical plating as described in the first embodiment. Some of the test gas sensor elements were also subjected to application of ac voltage for different periods of time in the manner as discussed in FIG. 7. The test gas sensor elements thus produced had 0 to 120 pores formed in a surface area of 1000 $\mu m^2$ of the target gas electrodes thereof whose diameters are within a range of 0.1 $\mu m$ to twice the thickness of the target gas electrode. The number of and the diameters of the pores were measured, like the measurement of the grain boundaries, by analyzing through an image recognizing device an image captured by an electron microscope. The number of the pores is found by sampling pores in four surface areas within a range of 1 mm×1 mm and averaging them.

Each of the test gas sensor elements was built in an oxygen sensor such as the one shown in FIG. 4 and installed in an exhaust system of an automotive engine. The engine was operated to discharge exhaust gasses of 400° C. to the exhaust system. An output of each of the test gas sensor elements was produced under feedback control and measured. The results of the measurements are plotted to define a curve 100 in a graph of FIG. 8. The ordinate axis indicates the feedback frequency of the outputs of the test gas sensor elements. The abscissa axis indicates the number of pores.

Additionally, the test gas sensor elements were also left in the exhaust gasses at 900° C. for 1000 hours. Afterwards, the voltages of outputs of the test gas sensor elements were measured. The results of the measurements are plotted to define a curve 200 in FIG. 8. The ordinate axis on the right side of FIG. 8 indicates the voltage levels of the outputs of the sensor elements.

Figure 8:
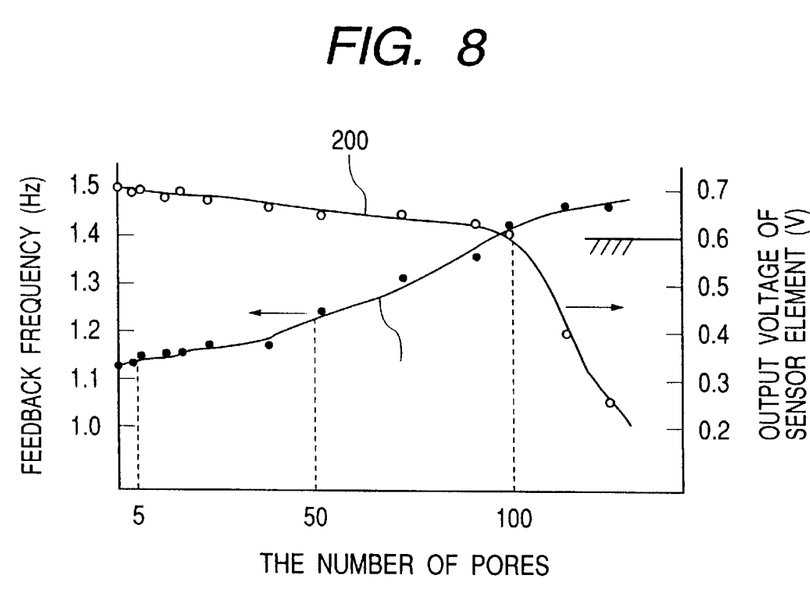
FIG. 8 is a graph which shows relations between a feedback frequency of a sensor output and the number of pores and between the voltage of a sensor output and the number of pores.

The graph shows that the feedback frequency of the outputs of the test gas sensor elements when the number of pores is less than five (5) is almost equal to that when the number of pores is zero (about 1.130 Hz), and the heat resistance decreases greatly when the number of pores exceeds 100. Note that the feedback frequency is about 1.132 Hz when the number of pores is four (4). It is, thus, found that the gas sensor elements have rapid responses and high heat resistances when the number of pores, as measured in the above manner, is within a range of 5 to 100.

The same measurements, as described above, were performed on the reference gas electrodes of the test gas sensor elements. Substantially the same results of the measurements were derived.

Figure 9:
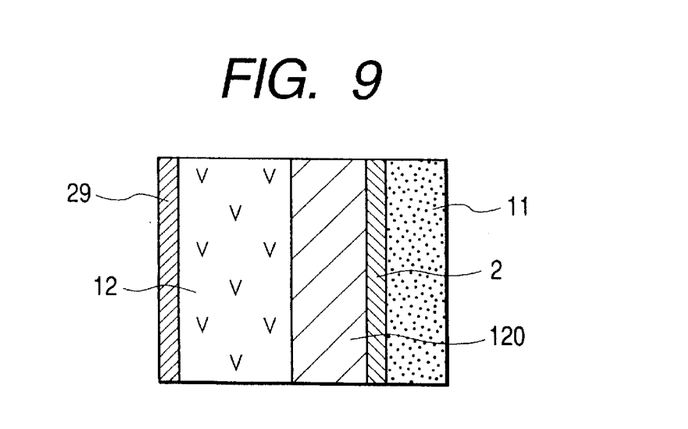
FIG. 9 is a vertical sectional view which shows a gas sensor element according to the third embodiment of the invention.

FIG. 9 shows a gas sensor element according to the third embodiment of the invention.

The solid electrolyte body 2 has a layer 120 changed in color. The layer 120 is in contact with the target gas electrode 2 and has a thickness of about 0.1 mm.

The discolored layer 120 is formed by applying a dc voltage to the gas sensor element through the target gas electrode 2 to increase the conductivity allowing electrons to flow therethrough. Specifically, the discolored layer 120 has a high thermal resistance and serves to keep the performance of the target gas electrode 2 even when the target gas electrode 2 is deteriorated by heat.

The discolored layer 120, however, has a long oxygen ion diffusion path which leads to a decrease in response speed of the gas sensor element. It is, thus, preferable that the thickness of the discolored layer 120 be within 0.2 mm.

A similar discolored layer of 0.2 mm or less in thickness may also be formed adjacent the reference gas electrode 29.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims. For example, the gas sensor element 1 may also be used in a gas sensor designed to measure the concentration of a component such as NOx, CO, or HC contained in exhaust gasses of automotive engines.

What is claimed is:

1. A gas sensor element comprising:

a solid electrolyte body;

a target gas electrode provided on a surface of said solid electrolyte body so as to be exposed to a gas to be measured; and a reference gas electrode provided on a surface of said solid electrolyte body so as to be exposed to a reference gas, wherein each of said target gas electrode and said reference gas electrode being made up of a plurality of crystal grains having grain boundaries between adjacent ones of said plurality of crystal grains such that a total length of the grain boundaries over each of said target gas electrode and said reference gas electrode is 1000 $\mu m$ or more in a respective electrode surface area of 1000 $\mu m^2$.

2. A gas sensor element as set forth in claim 1, wherein a number of pores formed in said target gas electrode whose diameters are within a range of 0.1 $\mu m$ to twice the thickness of said target gas electrode are 5 to 100 in a surface area of 1000 $\mu m^2$ of said target gas electrode.

3. A gas sensor element as set forth in claim 1, wherein a number of pores formed in said reference gas electrode whose diameters are within a range of 0.1 $\mu m$ to twice the thickness of said reference gas electrode are 5 to 100 in a surface area of 1000 $\mu m^2$ of said reference gas electrode.

4. A gas sensor element as set forth in claim 1, wherein a number of pores exist within grain boundaries of each of said target gas electrode and said reference gas electrode.

* * * * *